United States Patent
Queen

(10) Patent No.: US 7,479,473 B2
(45) Date of Patent: Jan. 20, 2009

(54) SOLVATED NONIONIC SURFACTANTS AND FATTY ACIDS

(75) Inventor: Craig B. Queen, Middletown, NJ (US)

(73) Assignee: Croda Uniqema, Inc., Chicago, IL (US)

(*) Notice: Subject to any disclaimer, the term of this patent is extended or adjusted under 35 U.S.C. 154(b) by 0 days.

(21) Appl. No.: 11/152,098

(22) Filed: Jun. 15, 2005

(65) Prior Publication Data

US 2005/0233929 A1   Oct. 20, 2005

Related U.S. Application Data

(63) Continuation of application No. 10/840,417, filed on May 7, 2004, now abandoned, which is a continuation-in-part of application No. 10/620,210, filed on Jul. 14, 2003, now abandoned.

(51) Int. Cl.
  *C11D 1/72*   (2006.01)
  *C11D 3/20*   (2006.01)
  *C11D 3/32*   (2006.01)

(52) U.S. Cl. ............... 510/126; 510/137; 510/138; 510/158; 510/159; 510/502; 510/505

(58) Field of Classification Search ............... None
See application file for complete search history.

(56) References Cited

U.S. PATENT DOCUMENTS

| 3,703,481 A | * | 11/1972 | Barker ............ 510/426 |
| 4,544,495 A | | 10/1985 | Schmolka |
| 5,700,772 A | | 12/1997 | Isobe et al. |
| 6,440,907 B1 | | 8/2002 | Santora et al. |
| 6,514,918 B1 | * | 2/2003 | Librizzi ............ 510/124 |
| 6,531,443 B2 | | 3/2003 | Perella et al. |
| 6,635,607 B2 | * | 10/2003 | Queen et al. ........ 510/124 |
| 6,750,192 B2 | | 6/2004 | Yamashita et al. |
| 6,770,607 B2 | | 8/2004 | Chen et al. |
| 2001/0027171 A1 | | 10/2001 | Sajac et al. |
| 2003/0036498 A1 | * | 2/2003 | Queen et al. ........ 510/499 |
| 2003/0091667 A1 | | 5/2003 | Gormley et al. |

FOREIGN PATENT DOCUMENTS

| EP | 0 842 655 | 5/1998 |
| JP | 08 337560 | 12/1996 |
| WO | WO 99/46356 | 9/1999 |
| WO | WO 02/092740 | 11/2002 |

* cited by examiner

*Primary Examiner*—Gregory R Del Cotto
(74) *Attorney, Agent, or Firm*—Jones Day

(57) ABSTRACT

A liquid and readily flowable composition includes (a) a room-temperature-solid solute, such as a nonionic surfactant, preferably having a hydrophile-lipophile balance from about 11.1 to about 18.4, a (ii) $C_8$-$C_{14}$ fatty acid, or combinations thereof; (b) an alkoxylated fatty alkanolamide; and (c) water, if needed. The alkoxylated fatty alkanolamide, which is substantially liquid at room temperature, solvates the solid solute to form a homogeneous composition which is liquid and readily flowable at room temperature. The select classes of nonionic surfactants include polyalkylene oxide carboxylic acid esters, ethoxylated fatty alcohols, poloxamers, alkyl polysaccharides, or combinations thereof. Useful alkoxylated fatty alkanolamides include propoxylated fatty ethanolamides.

26 Claims, No Drawings

SOLVATED NONIONIC SURFACTANTS AND FATTY ACIDS

CROSS REFERENCE TO RELATED APPLICATION

This application is a continuation of U.S. Ser. No. 10/840,417, filed May 7, 2004 now abandoned, which is a continuation-in-part of U.S. Ser. No. 10/620,210, filed Jul. 14, 2003 now abandoned. These applications, in their entirety, are incorporated herein by reference.

FIELD OF THE INVENTION

The present invention relates to solvating nonionic surfactants and fatty acids that are solid at room temperature with alkoxylated fatty alkanolamides and, at times, water. More specifically, the present invention relates to creating homogeneous solutions of these solid materials with propoxylated fatty ethanolamides.

BACKGROUND OF THE INVENTION

Nonionic surfactants have been incorporated in a plethora of compositions because of the wide variety of utilities, such as adjuvancy, thickening, foaming, emulsification, dispersion, coupling (increasing the compatibility of oils), solubilization, detergency, suspension, spreading, wetting and gelling. Although nonionic surfactants have been available for more than fifty years, only a limited number have been provided in a readily flowable liquid form. Solid nonionic surfactants are typically heated to melt the solid into a flowable form for subsequent incorporation into various formulations.

Such heating, however, is not only expensive, but may also affect other ingredients of the resulting formulations. For example, certain surfactants have the ability to solubilize water insoluble materials, for example fragrances which are frequently only oil-soluble materials, into aqueous systems by reducing surface tension of the solution or by reducing interfacial surface tension between non-compatible substances to disperse the materials therein. Incorporation of fragrances into melted surfactants may often result in loss of the fragrances, as many of these substances are volatile oils.

Solid fatty acids have also been used in a variety of applications, such as soaps, chemical intermediates for paints and coatings, fiber finish formulations, cleaning and personal care compositions, and lubricant applications. The solid fatty acids may also have to be heated to melt these solids for incorporation into liquid formulations. Such heating is similarly undesirable.

Alkoxylated fatty alkanolamides have been disclosed in U.S. Pat. No. 6,531,443. These alkoxylated fatty alkanolamides include capryl, stearic, soy oil and coconut oil fatty monoethanolamides and may be in liquid form. Liquid alkoxylated fatty alkanolamides have been used to solubilize other surfactants, including certain solid surfactants, as disclosed in U.S. Patent Application Publication No. US 2003/00364498 A1. Further, U.S. Patent Application Publication No. US 2003/0091667 A1 describes the solubilization of an antimicrobial composition and an alkoxylated fatty alkanolamide into a water phase to produce a visually clear and substantially colorless aqueous system. The antimicrobial composition includes halogenated hydroxyl-diphenyl ethers, for instance triclosan, which are solids at room temperature.

As used in colloidal chemistry and as used in surfactant chemistry, solubilization is the dispersion or emulsion of an insoluble material into a liquid, such as water or a predominately aqueous system. Such a dispersion or emulsion, however, does not result in a true or intimate solution, i.e., a uniform mixture of a solute and a solvent at the molecular or ionic level. The solubilized mixture is finely dispersed to produce a visually clear emulsion having discrete particles present on the microscopic or micron level. In other words, certain surfactants, such as the above-described alkoxylated fatty alkanolamides, have been used to finely disperse or solubilize water-insoluble materials into aqueous systems, i.e., systems having predominant amounts of water. Such systems, however, remain heterogeneous, dual or multiple phases on a microscopic level.

Further, many nonionic surfactants are described as being soluble or slightly soluble in water, typically less than ten weight percent. Such commonly used terminology, however, does not refer to the ability of the surfactants to form true aqueous solutions, but refers to the limits for the amounts of the surfactants suitable for aqueous dispersion or emulsification.

While various dispersions of alkoxylated fatty alkanolamides and surfactant systems or formulations containing alkoxylated fatty alkanolamides have been described, solvation of nonionic surfactants and fatty acids compositions that are solid at room temperature has remained elusive. Consequently, there is a need to solvate nonionic surfactants and fatty acids that are substantially solid at room temperature to provide a homogeneous liquid which is stable at room temperature. Desirably, such solvations will provide the known attributes of the solid nonionic surfactants and fatty acids, while providing the convenience of being liquid-form deliverable.

SUMMARY OF THE INVENTION

The present invention relates to the solvation of certain nonionic surfactants and fatty acids which are solid at ambient, room temperature (about 25° C.). Desirably, the solvation does not adversely affect the attribute for which the nonionic surfactant or the fatty acid is normally added to a composition or a formulation. In some cases, the solvation results in a synergistic affect where the solvated composition offers enhanced performance as compared to the use of an unsolvated nonionic surfactant.

More specifically, the present invention relates to a homogeneous liquid composition of nonionic surfactants or fatty acids, at least one alkoxylated fatty alkanolamide and, at times, water. In a preferred embodiment propoxylated fatty alkanolamides, more preferably propoxylated fatty ethanolamides are employed. Not all nonionic surfactants, however, may be effectively solvated by the alkoxylated fatty alkanolamides. Those surfactants of classes described herein preferably have a hydrophile-lipophile balance (HLB) about 11.1 to about 18.4. Nonionic surfactants having an HLB less than about 11.1 or greater than about 18.4, may not be completely solvated with the alkoxylated fatty alkanolamides used in the present invention.

Useful propoxylated fatty ethanolamides include propoxylated hydroxyethyl caprylamides, propoxylated hydroxyethyl cocamides, propoxylated hydroxyethyl linoleamides, propoxylated hydroxyethyl isostearamides, and combinations thereof.

DETAILED DESCRIPTION OF THE INVENTION

A large number of applications are contemplated by the present invention. Among the many applications in which the solvated compositions of the present invention may be incorporated include, without limitation, skin care products such as soap, liquid hand cleansers, body washes, facial washes, lotions, moisturizers, sun screens, and make-up; hair care products such as shampoos, conditioners, hair dyes and colorants and hair gels; industrial cleaners; household cleaners; laundry detergents; as well as pre-moistened towels such as baby wipes and geriatric wipes; agricultural products including pesticides; paints; textiles; metal cleaning products; metal working products; and lubricants.

As used herein to describe the present invention, and as used in general chemistry, the term solvation and its variants relate to the ability of a material (i.e., a solvent) to form a homogeneous liquid solution with another substance (i.e., a solute) through molecular interactions, but excluding substantial molecular dissociation of the solute, such as the case with sodium chloride being dissolved by water. In such a homogeneous solution the solute is dissolved by the solvent. In contrast, as described above, solubilization relates to the ability of a material (a solubilizer) to aid in the dispersion of two noncompatible, for example, immiscible, substances. Often the solubilizer reduces the interfacial surface tension between the immiscible substances to permit dispersion therebetween. Such a dispersion does not result in a homogeneous liquid solution, but merely results in a heterogeneous, often times finely dispersed micro-emulsion mixture. Thus, as used herein, the degree of homogeneity for solvated compositions exceeds the degree of homogeneity present in solubilized compositions. As used herein, a homogeneous composition refers to a uniform composition or true solution that does not separate into individual constituents over time at about room temperature, even when subjected to freezing and subsequent thawing.

Useful solvents with the practice of the present invention include alkoxylated fatty alkanolamides, preferably propoxylated fatty alkanolamides, and, at times, water. Solutes which may be solvated by such solvents include certain nonionic surfactants and fatty acids which are solid at room temperature. The nonionic surfactants that are solvated with the alkoxylated fatty alkanolamides include those classes of nonionic surfactants described below and preferably having a hydrophile-lipophile balance (HLB) about 11.1 to about 18.4.

The HLB is an indication of the weight amount of the hydrophilic portion of the nonionic surfactant. HLB values for most polyol fatty acid esters can be calculated with the formula HLB=20*(1−S/A), where S is the saponification number of the ester and A is the acid number of the recovered acid. Where the hydrophilic portion consists of ethylene oxide, the HLB value may be calculated with the formula HLB=E/5, where E is the weigh percent of oxyethylene content.

The solutes of the present invention are those that are solid at room temperature and selected from
(a) nonionic surfactants preferably having an HLB from about 11.1 to about 18.4 and selected from the following classes:
(1) polyalkylene oxide carboxylic acid esters having from about 8 to about 30 carbon atoms and having a polyethylene oxide moiety corresponding to the formula —$(OCH_2CH_2)_n$, where n is from about 5 to about 200, and further where both mono- and di-esters are included, and preferably having from about 16 to about 18 carbon atoms and where n is from about 8 to about 150;
(2) ethoxylated fatty alcohols having an ethylene oxide moiety corresponding to the formula —$(OCH_2CH_2)_m$, wherein m is from about 5 to about 150, preferably from about 6 to about 31, and more preferably from about 7 to about 21 moles of ethoxylation, and having a fatty alcohol moiety having from about 6 to about 30 carbon atoms, preferably from about 8 to about 22 carbon atoms, and more preferably from about 10 to about 19 carbon atoms, where these fatty alcohols can be straight or branched chain alcohols and can be saturated or unsaturated, and where non-limiting examples of suitable ethoxylated fatty alcohols include oleth-10 through oleth-20, which are ethylene glycol ethers of oleth alcohol, wherein the numeric designation indicates the number of ethylene oxide moieties present, the steareth series of compounds such as steareth-10 through steareth-21, which are ethylene glycol ethers of steareth alcohol, wherein the numeric designation indicates the number of ethylene oxide moieties present, and other fatty alcohols may include lauryl alcohol and isocetyl alcohol;
(3) poloxamers, which are ethylene oxide and propylene oxide block copolymers, having from about 15 to about 100 moles of ethylene oxide, preferably, about 60 to about 70 moles, and having about 15 to about 70 moles of propylene oxide, preferably, about 20 to about 30 moles;
(4) alkyl polysaccharide (APS) surfactants (e.g. alkyl polyglycosides) having a hydrophobic group with about 6 to about 30 carbon atoms and a polysaccharide (e.g., polyglycoside) as the hydrophilic group; optionally, there can be a polyalkylene-oxide group joining the hydrophobic and hydrophilic moieties; and the alkyl group (i.e., the hydrophobic moiety) can be saturated or unsaturated, branched or unbranched, and unsubstituted or substituted (e.g., with hydroxy); and
(b) carboxylic fatty acids of the formula $R^3COOH$ where a mean average $R^3$ is from about 8 to about 14 carbon atoms, which can be saturated or unsaturated, and preferably from about 12 to about 14 carbon atoms; and
(c) combinations thereof.

Preferred solutes are polyalkylene oxide carboxylic acid esters, ethoxylated fatty alcohols, carboxylic fatty acids, and combinations thereof.

The amount of solute present in the homogeneous compositions of the present invention may vary from low concentrations, for example about 10 weight percent or less, to high concentrations, for example about 80 weight percent or greater, where the weight percents are on a total composition basis. The amount of the above-described nonionic surfactants that may be solvated depends upon several factors, including the HLB of the nonionic surfactant to be solvated. Other factors may include the particular solvent, including water, if present. At terminal ends of the preferred HLB range, i.e., about 11.1 and about 18.4, about 10 weight percent nonionic surfactant may suitably be solvated. Solutions having less than 10 weight percent nonionic surfactant may also be formed, but these more dilute solutions are not preferred as functionality of the surfactant may be diluted. Higher amounts of nonionic surfactants may be solvated at HLB values between the 11.1 and 18.4 values. For example, about 80 weight percent or greater of nonionic surfactants having an HLB from about 15 to about 17 may be solvated. Accordingly, the true solutions of room-temperature-solid nonionic surfactants having HLB values between about 11.1 and about 18.4 values may be formed having from about 10 weight percent to about 80 weight percent nonionic surfactant on a total composition basis, preferably from about 20 weight percent to about 70 weight percent, and more generally from about 20 weight percent to about 65 weight percent.

As noted in Examples 1 through 14, solvation levels for certain nonionic surfactants with propoxylated fatty ethanolamides vary with HLB of the nonionic surfactants, and, at times, water. Numerous testing was done at less than the maximum solvation limits to confirm the homogeneity of the resulting compositions at varying concentrations of solute and solvent. Nonionic surfactants having a HLB of less than about 11.1 tend to form cloudy or hazy mixtures with possible phase separation. Nonionic surfactants having a HLB of greater than about 18.4 tend to be cloudy or hazy mixtures with possible phase separation and possible solidification.

The above-described solvation levels may also suitably be used for blends or combinations of nonionic surfactants, whereby the resulting HLB of the nonionic surfactant blend is preferably within from about 11.1 to about 18.4. Thus, a blend of a nonionic surfactant having a HLB from about 11.1 to about 18.4 and another nonionic surfactant, which may or may not have a HLB from about 11.1 to about 18.4, may suitably be solvated, provided that the combined HLB is from about 11.1 to about 18.4. Preferably, only minor amounts of nonionic surfactants outside of the HLB range of about 11.1 to about 18.4 are included in surfactant blends to be solvated.

Solvation levels for the nonionic surfactants also depend upon the amount of solvent used. Alkoxylated fatty alkanolamides in the amounts from about 10 weight percent to about 80 weight percent on a total combination basis may be present in the solvated compositions of the present invention, preferably from about 20 weight percent to about 70 weight percent, and more preferably from about 20 weight percent to about 65 weight percent. Some water is required for solvation of the nonionic surfactants with alkoxylated fatty alkanolamides to form homogeneous liquid solutions. Generally, at least 5 weight percent water is used for forming homogeneous liquid compositions with nonionic surfactants. The homogeneous liquid compositions may suitably contain from about 5 weight percent to about 35 weight percent water on a total composition basis, preferably from about 10 to about 30 weight percent water, more preferably from about 20 to about 30 weight percent water.

Solvations of the above-described carboxylic $C_8$-$C_{14}$ fatty acid solutes do not require the addition of water. Solvations having of about 50 weight percent carboxylic fatty acid solutes are achieved with about 50 weight percent alkoxylated fatty alkanolamides solvents, where the weight percents are on a total composition basis. Increased amounts of the alkoxylated fatty alkanolamides solvents may suitably be used to form clear, homogeneous solutions of the room-temperature-solid carboxylic fatty acid solutes. Useful, nonlimiting examples of fatty acid solutes include lauric acid, myristic fatty acid, and coconut fatty acid.

The fatty moiety of the alkoxylated fatty alkanolamide is preferably a branched or straight chain, alkyl or alkenyl group containing 3 to 21 carbon atoms, more preferably containing 8 to 18 carbon atoms, or combinations thereof. The alkoxy moiety may be an ethoxy, propoxy, or butoxy group, or combinations thereof. In a preferred embodiment propoxylated fatty alkanolamides, more preferably propoxylated fatty ethanolamides are employed.

Useful alkoxylated fatty alkanolamide solvents are those represented by Formula 1;

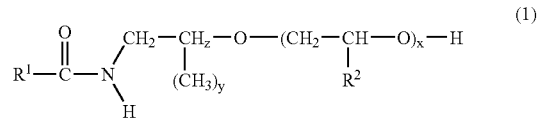

where
R$^1$ is a branched or straight chain, saturated or unsaturated C$_3$-C$_{21}$ alkyl radical, preferably a C$_8$-C$_{18}$ alkyl radical, or a combination thereof; R$^2$ is a C$_1$-C$_2$ alkyl radical or a combination thereof, preferably R$^2$ is a C$_1$ alkyl radical; x is from about 1 to about 8, preferably about 1 to about 5, and more preferably from about 1 to about 3; y is 0 or 1, preferably 0; and z is 1 or 2, preferably 2.

Examples of useful alkoxylated-fatty alkanolamides include polyoxypropylene-, polyoxybutylene-, fatty ethanolamides or fatty isopropanolamides. Alkoxylated fatty ethanolamides are preferred, particularly propoxylated fatty ethanolamides. The fatty ethanolamide moiety is preferably a fatty monoethanolamide, and more preferably is derived from lauric monoethanolamide, capric monoethanolamide, caprylic monoethanolamide, caprylic/capric monoethanolamide, decanoic monoethanolamide, myristic monoethanolamide, palmitic monoethanolamide, stearic monoethanolamide, isostearic monoethanolamide, oleic monoethanolamide, linoleic monoethanolamide, octyidecanoic monoethanolamide, 2-heptylundecanoic monoethanolamide, coconut oil fatty monoethanolamide, beef tallow fatty monoethanolamide, soy oil fatty monoethanolamide and palm kernel oil fatty monoethanolamide. Of these capryl, linoleyl, stearic, isostearic, soy oil, and coconut oil fatty monoethanolamides are preferred. And when isostearic is used it is preferably used in combination with another of the alkoxylated fatty alkanolamides. (The ratios are described below in paragraph [0031].)

Preferred propoxylated fatty ethanolamides include propoxylated hydroxyethyl caprylamides, propoxylated hydroxyethyl cocamides, propoxylated hydroxyethyl linoleamides, propoxylated hydroxyethyl isostearamides, and combinations thereof. Propoxylated hydroxyethyl cocamides are more preferred. Preferred specific materials are PPG-1 hydroxyethyl caprylamide, PPG-2 hydroxyethyl cocamide, PPG-3 hydroxyethyl linoleamide, PPG-2 hydroxyethyl isostearamide, and combinations thereof. PPG-2 hydroxyethyl cocamide is particularly preferred.

In an alternative embodiment, alkoxylated fatty isopropanolamides are employed. The fatty isopropanolamide moiety is preferably a fatty monoisopropanolamide, and more preferably is derived from lauric monoisopropanolamide, capric monoisopropanolamide, caprylic monoisopropanolamide, caprylic/capric monoisopropanolamide, decanoic monoisopropanolamide, myristic monoisopropanolamide, palmitic monoisopropanolamide, stearic monoisopropanolamide, isostearic monoisopropanolamide, oleic monoisopropanolamide, linoleic monoisopropanolamide, octyldecanoic monoisopropanolamide, 2-heptylundecanoic monoisopropanolamide, coconut oil fatty monoisopropanolamide, beef tallow fatty monoisopropanolamide, soy oil fatty monoisopropanolamide, and palm kernel oil fatty monoisopropanolamide. Of these, stearic, isostearic, and coconut oil fatty monoisopropanolamide are preferred.

A method for solvating a room-temperature-solid solute according to the present invention comprises the steps of (a) providing a room-temperature-solid solute selected from the group consisting of a nonionic surfactant preferably having a hydrophile-lipophile balance from about 11.1 to about 18.4, a $C_8$-$C_{14}$ fatty acid, and combinations thereof; (b) selecting an alkoxylated fatty alkanolamide which is liquid at room temperature, (c) combining the solute, optionally the water, and the alkoxylated fatty alkanolamide; (d) heating the mixture to a temperature greater than the pour point of the solute to liquefy the solid; and (e) maintaining temperature of the mixture and stirring until a homogeneous liquid composition is achieved. The composition may be cooled to room temperature to form a room-temperature, homogenous liquid composition. The present invention, however, is not limited to heating the combined mixture for liquefaction of the solute. For example, any of the constituents may be heated, individually or in combination, to provide sufficient enthalpy to melt the solid solute and to keep the resultant mixture in liquid form during mixing. The heating may be done prior, during or after combining the different constituents.

The solvation techniques of the present invention provide a liquid and readily flowable composition comprising (a) a room-temperature-solid solute selected from the group consisting of (i) a nonionic surfactant, such as polyalkylene oxide carboxylic acid esters, ethoxylated fatty alcohols, poloxamers, alkyl polysaccharides, and combinations thereof, preferably having a hydrophile-lipophile balance from about 11.1 to about 18.4, (ii) a $C_8$-$C_{14}$ fatty acid, or combinations thereof; and (b) an alkoxylated fatty alkanolamide composition; or combinations of alkoxylated fatty alkanolamides and optionally (c) water, when needed.

When the solute comprises a polyalkylene oxide carboxylic acid diester, the use of a solvent comprising a propoxylated hydroxyethyl isostearamide in combination with another propoxylated hydroxyethyl alkylamide, such as propoxylated hydroxyethyl caprylic/capric amide or polypropylene glycol hydroxyethyl cocamide, and water results in a synergistic thickening effect. By synergistic is meant the resultant thickening is greater than the thickening caused by the solute alone or the solvent alone. Such synergistic thickening is useful in cleansing formulations, for example, but not limited to, shampoos. For example, as described in Examples 15 and 16, a solvated composition according to the present invention, which contained a commonly used thickener as a solute, has enhanced thickening over the solute alone and over the solvent alone for three different adult shampoo bases and for a baby shampoo formulation. The solute used was a polyoxyethylene (150) distearate. The solvent used was an isostearamide/nonisostearamide combination. The solvated composition included the polyoxyethylene (150) distearate solute solvated with the isostearamide/nonisostearamide solvent which salvation surprisingly had increased thickening over the contributions of its individual constituents.

For synergistic thickening, the amount of the isostearamide component in the isostearamide/nonisostearamide solvent may suitably vary from about 5 to about 95 weight percent on a solvent basis, preferably from about 10 to about 60 weight percent, and more preferably from about 15 to about 35 weight percent.

In an alternative embodiment, a synergistic thickening effect is also obtained with a solute comprising a polyalkylene oxide carboxylic acid diester, the use of a solvent comprising a propoxylated hydroxyethyl cocamide, and water. The propoxylated hydroxyethyl cocamide is preferably present in the amounts from about 5 weight percent to about 50 weight percent on a total combination basis in the solvated compositions of the present invention, preferably from about 10 weight percent to about 35 weight percent, and more preferably from about 15 weight percent to about 25 weight percent. The polyalkylene oxide carboxylic acid diester is preferably present in the amounts from about 20 weight percent to about 70 weight percent on a total combination basis, preferably from about 30 weight percent to about 60 weight percent, and more preferably from about 45 weight percent to about 55 weight percent. The homogeneous liquid compositions suitably contain from about 5 weight percent to about 50 weight percent water on a total composition basis, preferably from about 15 to about 40 weight percent water, more preferably from about 25 to about 30 weight percent water. A particularly surprising feature is that relatively high concentrations of polyalkylene oxide carboxylic acid diester can be solvated using relatively low concentrations of propoxylated hydroxyethyl cocamide.

In one aspect of the present invention, a shampoo is provided which comprises, i.e. is formed from a liquid and readily flowable composition defined herein, and additionally comprises an anionic surfactant; and optionally one or more of a betaine, a non-ionic surfactant, an amphoteric surfactant, and a cationic surfactant.

In a further aspect a baby shampoo is provided. The baby shampoo comprises (i) a room-temperature liquid and solvated thickening composition comprising (a) a solvent comprising an alkoxylated fatty alkanolamide; preferably a propoxylated hydroxyethyl isostearamide, a propoxylated hydroxyethyl caprylamide, a propoxylated hydroxyethyl cocamide, and combinations thereof; more preferably a propoxylated hydroxyethyl cocamide, (b) a solute comprising a room-temperature-solid nonionic surfactant comprising polyalkylene oxide carboxylic acid diesters having a polyethylene oxide moiety corresponding to the formula of $(-OCH_2CH_2)_n$, where n is from about 5 to about 200, and having a carboxylic acid moiety from about 8 to about 30 carbon atoms, and preferably having a hydrophile-lipophile balance from about 11.1 to about 18.4; and (c) water; (ii) an anionic surfactant; (iii) a betaine; (iv) a nonionic surfactant; and (v) optionally, an amphoteric surfactant. Preferably, the anionic surfactant is present from about 2 to about 5 weight percent on a total shampoo basis; the betaine is present from about 3 to about 6 weight percent on a total shampoo basis; the nonionic surfactant is present from about 6 to about 10 weight percent on a total shampoo basis; and the amphoteric surfactant is present from about 0 to about 5 weight percent on a total shampoo basis. Non-limiting examples of anionic surfactants useful for baby shampoos include sodium trideceth sulfate. Non-limiting examples of betaines useful for baby shampoos include cocamidopropyl betaine. Non-limiting examples of nonionic surfactants useful for baby shampoos include PEG sorbitan laurate. Non-limiting examples of amphoteric surfactants useful for baby shampoos includes sodium laureth sulfate.

In another aspect of the present invention an adult shampoo is provided. The adult shampoo comprises (i) a room-temperature liquid and solvated thickening composition comprising: (a) a solvent comprising an alkoxylated fatty alkanolamide; preferably a propoxylated hydroxyethyl isostearamide, a propoxylated hydroxyethyl caprylamide, a propoxylated hydroxyethyl cocamide, and combinations thereof; more preferably a propoxylated hydroxyethyl cocamide, (b) a solute comprising a room-temperature-solid nonionic surfactant comprising polyalkylene oxide carboxylic acid diesters having a polyethylene oxide moiety corresponding to the formula of $(-OCH_2CH_2)_n$, where n is from about 5 to about 200, and having a carboxylic acid moiety from about 8 to about 30 carbon atoms, and preferably having a hydrophile-lipophile balance from about 11.1 to about 18.4; and (c) water; (ii) anionic surfactant; (iii) betaine; (iv) nonionic surfactant; and (v) optionally, cationic surfactant. Preferably, the anionic surfactant is present from about 6 to about 15 weight percent on a total shampoo basis; the betaine is present from about 2 to about 6 weight percent on a total shampoo basis; the nonionic surfactant is present from about 1 to about 4 weight percent on a total shampoo basis; and the cationic surfactant is present from about 0 to about 1 weight percent on a total shampoo basis. Non-limiting examples of anionic surfactants useful for adult shampoos include sodium laureth sulfate, sodium lauryl sulfate, ammonium laureth sulfate, ammonium lauryl sulfate, alpha-olefin sulfonate, and combinations thereof. Non-limiting examples of betaine useful for adult shampoos include cocamidopropyl betaine. Non-limiting examples of nonionic surfactants useful for adult shampoos include cocamide MEA, lauramide DEA, PPG-2 hydroxyethyl coco/isostearamide, and combinations thereof. Non limiting examples of cationic surfactants useful for adult shampoos includes Polyquat-10 or behentrimonium chloride.

In another aspect of the present invention an industrial cleaning composition, preferably a laundry detergent is provided. The industrial cleaning composition comprises:
(i) a liquid and readily flowable composition comprising:
  a) a room-temperature-solid solute selected from the group consisting of a nonionic surfactant, a $C_8$-$C_{14}$ fatty acid, and combinations thereof;
  b) an alkoxylated fatty alkanolamide; and
  c) optionally water;
wherein the alkoxylated fatty alkanolamide acts as a solvent to solvate the solid solute to form a homogeneous composition which is liquid and readily flowable at room temperature; and
(ii) at least one surfactant selected from the group consisting of an anionic surfactant; a non-ionic surfactant, an amphoteric surfactant, and a cationic surfactant.

The features and advantages of the present invention are more fully shown by the following examples which are provided for purposes of illustration, and are not to be construed as limiting the invention in any way.

EXAMPLES

Examples 1 through 14 demonstrate the ability of alkoxylated fatty alkanolamides to solvate selected room-temperature-solid materials. The selected room-temperature-solid materials were combined with an alkoxylated fatty alkanolamide composition having 1 part by weight propoxylated hydroxyethyl isostearamide to 3 parts by weight propoxylated hydroxyethyl cocamide (Composition A) and, optionally, water at various concentrations.

The solid materials in Examples 1-14 were added to Composition A and heated to a temperature of 50° C. or to a temperature slightly greater than their melting or pour point when it exceeded 50° C. to provide a liquefied material. The material was stirred in a vessel with a mixing blade while maintaining temperature until homogeneous. Water was separately heated to a temperature of about 50° C. The heated water, if any, was added to the blend with moderate stirring. The resulting mixtures were cooled to room temperature.

Example 1

Polyoxyethylene (20) isohexadecyl ether (Arlasolve 200, available from Uniqema) has a HLB of about 15.7, is a solid at room temperature (34° C. pour point). The polyoxyethylene (20) isohexadecyl ether was combined with Composition A and water at various proportions according to the procedures described above. Solvated, clear and homogeneous compositions were observed at varying concentrations of the three ingredients. Some water, however, was required for salvation. The results are shown below in Table 1

TABLE 1

| polyoxyethylene (20) isohexadecyl ether, Wt. % | Composition A, Wt. % | Water, Wt. % | Appearance at 20° C. |
|---|---|---|---|
| 38 | 12 | 50 | clear soluble gel |
| 20 | 65 | 15 | clear, soluble, pourable |
| 40 | 40 | 20 | clear, soluble, pourable |
| 50 | 30 | 20 | clear, soluble, pourable |
| 60 | 20 | 20 | clear, soluble, pourable |
| 50 | 50 | 0 | cloudy homogeneous solid |
| 60 | 40 | 0 | cloudy homogeneous solid |
| 70 | 30 | 0 | homogeneous solid |
| 75 | 25 | 0 | homogeneous solid |

Example 2

Polyoxyethylene (23) lauryl ether (Brij 35, available from Uniqema) has a HLB of about 16.9, is a solid at room temperature (33° C. pour point). The polyoxyethylene (23) lauryl ether was combined with Composition A and water at various proportions according to the procedures described above. Solvated, clear and homogeneous compositions were observed at varying concentrations of the three ingredients. Some water, however, was required for solvation. The results are shown below in Table 2.

TABLE 2

| polyoxyethylene (23) lauryl ether, Wt. % | Composition A, Wt. % | Water, Wt. % | Appearance at 20° C. |
|---|---|---|---|
| 20 | 65 | 15 | clear, soluble |
| 44 | 14 | 42 | clear, soluble, gel |
| 60 | 20 | 20 | clear, soluble |
| 75 | 25 | 0 | cloudy homogeneous solid |

Example 3

Polyoxyoxyethylene (20) isohexadecyl ether of Example 1 and the polyoxyethylene (23) lauryl ether of Example 2 were combined with Composition A and water at various proportions according to the procedures described above. Solvated, clear and homogeneous compositions were observed at varying concentrations of the three ingredients. The results are shown below in Table 3A.

TABLE 3A

| polyoxyethylene (20) isohexadecyl ether, Wt. % | polyoxyethylene (23) lauryl ether, Wt. % | Composition A, Wt. % | Water, Wt. % | Appearance at 20° C. |
|---|---|---|---|---|
| 50 | 10 | 20 | 20 | clear, soluble, pourable |
| 10 | 50 | 20 | 20 | clear, soluble, pourable |

The HLB of the combined ethers was calculated to be 15.9 and 16.7 for the polyoxyethylene (20) isohexadecyl ether rich and lean combinations, respectively. The polyoxyethylene (23) lauryl ether rich composition was formulated to be an effective liquid nonionic foaming surfactant blend.

An effective nonionic foaming surfactant blend was also made using a different solvent from Composition A. A propoxylated hydroxyethyl caprylamide (Promidium CC product available from Uniqema, Composition D) solvated the polyoxyethylene (20) isohexadecyl ether and the polyoxyethylene (23) lauryl ether combination with the presence of some water according to the procedures described above. Solvated, clear and homogeneous composition was observed. The results are shown below in Table 3B.

TABLE 3B

| polyoxyethylene (20) isohexadecyl ether, Wt. % | polyoxyethylene (23) lauryl ether, Wt. % | Composition D, Wt. % | Water, Wt. % | Appearance at 20° C. |
|---|---|---|---|---|
| 10 | 50 | 20 | 20 | clear, soluble, pourable |

Example 4

Polyoxyethylene (2) stearyl ether (Brij 72, available from Uniqema) has a HLB of about 4.9, is a solid at room temperature (43° C. pour point). The polyoxyethylene (2) stearyl ether was combined with Composition A and water according to the procedures described above. A solvated, clear and homogeneous composition was not obtained. The results are shown below in Table 4.

TABLE 4

| polyoxyethylene (2) stearyl ether, Wt. % | Composition A, Wt. % | Water, Wt. % | Appearance at 20° C. |
|---|---|---|---|
| 20 | 65 | 15 | solid, separation |

Example 5

Polyoxyethylene (10) stearyl ether (Brij 76, available from Uniqema) has a HLB of about 12.4, is a solid at room temperature (38° C. pour point). The polyoxyethylene (10) stearyl ether was combined with Composition A and water at various proportions according to the procedures described above. Solvated, clear and homogeneous compositions were observed. Some water, however, was required for salvation. The results are shown below in Table 5.

TABLE 5

| polyoxyethylene (10) stearyl ether, Wt. % | Composition A, Wt. % | Water, Wt. % | Appearance at 20° C. |
|---|---|---|---|
| 20 | 65 | 15 | clear, soluble |
| 60 | 20 | 20 | homogeneous, cloudy gel |

Example 6

Polyoxyethylene (20) stearyl ether (Brij 78, available from Uniqema) has a HLB of about 15.3, is a solid at room temperature (38° C. pour point). The polyoxyethylene (20) stearyl ether was combined with Composition A and water at various proportions according to the procedures described above. Solvated, clear and homogeneous compositions were observed. The results are shown below in Table 6.

TABLE 6

| polyoxyethylene (20) stearyl ether, Wt. % | Composition A, Wt. % | Water, Wt. % | Appearance at 20° C. |
|---|---|---|---|
| 40 | 40 | 20 | clear, soluble, pourable |
| 45 | 45 | 10 | homogeneous, cloudy solid |
| 20 | 65 | 15 | stable liquid, slight haze |

Example 7

Polyoxyethylene (100) stearyl ether (Brij 700, available from Uniqema) has a HLB of about 18.8, is a solid at room temperature (55° C. pour point). The polyoxyethylene (100) stearyl ether was combined with Composition A and water at various proportions according to the procedures described above. Solvated, clear and homogeneous compositions were not observed at varying concentrations of the three ingredients. The results are shown below in Table 7.

TABLE 7

| polyoxyethylene (100) stearyl ether, Wt. % | Composition A, Wt. % | Water, Wt. % | Appearance at 20° C. |
|---|---|---|---|
| 16 | 52 | 32 | cloudy homogeneous high viscosity |
| 22 | 72 | 6 | cloudy homogeneous solid |
| 21 | 68 | 11 | cloudy homogeneous solid |
| 40 | 40 | 20 | cloudy homogeneous solid |
| 20 | 65 | 15 | separation |
| 19 | 62 | 19 | separation |

Example 8

Polyoxyethylene (21) stearyl ether (Brij 721, available from Uniqema) has a HLB of about 15.5, is a solid at room temperature (45° C. pour point). The polyoxyethylene (21) stearyl ether was combined with Composition A and water at various proportions according to the procedures described above. Solvated, clear and homogeneous compositions were observed. The results are shown below in Table 8.

TABLE 8

| polyoxyethylene (21) stearyl ether, Wt. % | Composition A, Wt. % | Water, Wt. % | Appearance at 20° C. |
|---|---|---|---|
| 53 | 17 | 30 | clear gel |
| 60 | 20 | 20 | clear gel |
| 19 | 62 | 19 | clear, soluble liquid |

Example 9

Polyoxyethylene (20) oleyl ether (Brij 98, available from Uniqema) has a HLB of about 15.3, is a solid at room temperature (23° C. pour point). The polyoxyethylene (20) oleyl ether was combined with Composition A and water according to the procedures described above. Solvated, clear and homogeneous compositions were observed. The results are shown below in Table 9.

TABLE 9

| polyoxyethylene (20) oleyl ether, Wt. % | Composition A, Wt. % | Water, Wt. % | Appearance at 20° C. |
|---|---|---|---|
| 20 | 65 | 15 | clear, soluble, pourable |

Example 10

Polyoxyethylene (40) stearate (Myrj 52, available from Uniqema) has a HLB of about 16.9, is a solid at room temperature (38° C. pour point). The polyoxyethylene (40) stearate was combined with Composition A and water at various proportions according to the procedures described above. Solvated, clear and homogeneous compositions were observed at varying concentrations of the three ingredients. The results are shown below in Table 10.

TABLE 10

| polyoxyethylene (40) stearate, Wt. % | Composition A, Wt. % | Water, Wt. % | Appearance at 20° C. |
|---|---|---|---|
| 21 | 68 | 11 | clear, soluble, pourable |
| 19 | 62 | 19 | clear, soluble, pourable |
| 24 | 76 | 0 | cloudy homogeneous solid |
| 16 | 52 | 32 | separation |
| 20 | 65 | 15 | stable with haze |

Example 11

Polyoxyethylene (50) stearate (Myrj 53, available from Uniqema) has a HLB of about 17.9, is a solid at room temperature (40° C. pour point). The polyoxyethylene (50) stearate was combined with Composition A and water according to the procedures described above. Solvated, clear and homogeneous compositions were observed. The results are shown below in Table 11.

TABLE 11

| polyoxyethylene (50) stearate, Wt. % | Composition A, Wt. % | Water, Wt. % | Appearance at 20° C. |
|---|---|---|---|
| 20 | 65 | 15 | clear, soluble, pourable |

Example 12

Polyoxyethylene (100) stearate. (Myrj 59, available from Uniqema) has a HLB of about 18.8, is a solid at room temperature (46° C. pour point). The polyoxyethylene (100) stearate was combined with Composition A and water at various proportions according to the procedures described above. Solvated, clear and homogeneous compositions were not observed. The results are shown below in Table 12.

TABLE 12

| polyoxyethylene (100) stearate, Wt. % | Composition A, Wt. % | Water, Wt. % | Appearance at 20° C. |
|---|---|---|---|
| 22 | 72 | 6 | cloudy homogeneous solid |
| 20 | 65 | 15 | separation |
| 21 | 68 | 11 | separation |
| 16 | 52 | 32 | separation |

Example 13

Polyoxyethylene (20) sorbitan tristearate (Tween 65, available from Uniqema) has a HLB of about 10.5, is a solid at room temperature (33° C. pour point). The polyoxyethylene (20) sorbitan tristearate was combined with Composition A and water according to the procedures described above. Solvated, clear and homogeneous compositions were not observed. The results are shown below in Table 13.

TABLE 13

| polyoxyethylene (20) sorbitan tristearate, Wt. % | Composition A, Wt. % | Water, Wt. % | Appearance at 20° C. |
|---|---|---|---|
| 20 | 65 | 15 | gross separation |

Example 14

Polyoxyethylene (150) distearate (Composition C) (Estol 3734, available from Uniqema) has a HLB of about 18.4, is a solid at room temperature (55° C. pour point). Composition C was combined with Composition A and water at the proportions described below and according to the procedures described above to form Composition B. Composition B was observed to be a solvated, clear and homogeneous composition. The results are shown below in Table 14.

TABLE 14

| polyoxyethylene (150) distearate, Wt. % | Composition A, Wt. % | Water, Wt. % | Appearance at 20° C. |
|---|---|---|---|
| 20 | 65 | 15 | clear, soluble, pourable |

Example 15

Adult shampoo bases were prepared at (1) 7:3 ratios of sodium laureth sulfate (SLES) to cocoamidopropyl betaine (CAB); (2) 7:3 ratios of ammonium lauryl ether sulfate (ALES) to ammonium lauryl sulfate (ALS); and (3) at 7:3 ratios of alpha olefin sulfonates (AOS) to cocoamidopropyl betaine (CAB). Compositions B (i.e., the solvated polyoxyethylene (150) distearate solution) and C (i.e., polyoxyethylene (150) distearate) of Example 14 were added to the adult shampoo bases. Composition A was also added to the shampoo bases for comparison.

Viscosity in centipoise (cPs) were measured with a Brookfield DVII model viscometer according to standard operating procedures provided by the manufacturer to obtain reliable viscosity measurement over wide ranges of viscosity. The viscosity results of the resulting compositions in centipoise are listed below.

TABLE 15A

SLES/CAB Shampoo Base at 0.2% NaCl

| Wt. % Composition Added | Viscosity, cPs, for Compositions: | | |
|---|---|---|---|
| | A | B | C |
| 1.0 | 19 | 5,963 | 21 |
| 2.0 | 45 | 226,000 | 242 |
| 3.0 | 186 | 267,000 | 3,419 |

TABLE 15B

ALES/ALS Shampoo Base at 0.4% NaCl

| Wt. % Composition Added | Viscosity, cPs, for Compositions: | | |
|---|---|---|---|
| | A | B | C |
| 1.0 | 8 | 28 | 5.4 |
| 2.0 | 13 | 424 | 7.5 |
| 3.0 | 24 | 8,278 | 8.4 |

TABLE 15C

AOS/CAB Shampoo Base at 0.2% NaCl

| Wt. % Composition Added | Viscosity, cPs, for Compositions: | | |
|---|---|---|---|
| | A | B | C |
| 1.0 | 5.4 | 10 | 5.4 |
| 2.0 | 6.5 | 28 | 6.5 |
| 3.0 | 9.6 | 14,637 | 9.6 |

For comparison, the results of Tables 15A-15C are shown below in Table 15D for compositions B and C on a percent-added polyoxyethylene (150) distearate basis.

TABLE 15D

Thickener Comparison On a Polyoxyethylene (150) Distearate Basis

| Wt. % Composition Added | Wt. % PEG (150) Distearate Added | Viscosity, cPs, for Compositions | | Shampoo Base |
|---|---|---|---|---|
| | | B | C | |
| 1.0 | 1.0 | | 21 | 1 |
| 2.0 | 2.0 | | 242 | 1 |
| 3.0 | 3.0 | | 3,419 | 1 |
| 1.0 | 0.2 | 5,963 | | 1 |
| 2.0 | 0.4 | 226,000 | | 1 |
| 3.0 | 0.6 | 267,000 | | 1 |
| 1.0 | 1.0 | | 5.4 | 2 |
| 2.0 | 2.0 | | 7.5 | 2 |
| 3.0 | 3.0 | | 8.4 | 2 |
| 1.0 | 0.2 | 28 | | 2 |
| 2.0 | 0.4 | 424 | | 2 |
| 3.0 | 0.6 | 8,278 | | 2 |
| 1.0 | 1.0 | | 5.4 | 3 |
| 2.0 | 2.0 | | 6.5 | 3 |
| 3.0 | 3.0 | | 9.6 | 3 |
| 1.0 | 0.2 | 10 | | 3 |
| 2.0 | 0.4 | 28 | | 3 |
| 3.0 | 0.6 | 14,637 | | 3 |

1 SLES/CAB Shampoo Base at 0.2% NaCl
2 ALES/ALS Shampoo Base at 0.4% NaCl
3 AOS/CAB Shampoo Base at 0.2% NaCl Composition B showed unexpected results over Composition C, as noted by the viscosity increase for the same levels of polyoxyethylene (150) distearate.

Example 16

A baby shampoo formulation was prepared as described in Table 16A below.

TABLE 16A

Uniqema Baby Shampoo Formulation

| Component | Wt. % |
|---|---|
| Water | 85.0 |
| Atlas G-4280 (PEG-80 Sorbitan Laurate) | 4.5 |
| Standapol ES-2 (Sodium Laureth Sulfate) | 2.0 |
| Cedapal TD-407 (Sodium Trideceth Sulfate) | 3.0 |
| Monateric CAB-LC (Cocoamidopropyl Betaine) | 4.0 |
| Pricerine 9088 (Glycerine) | 1.5 |
| Preservative | qs |
| Fragrance | qs |

Compositions B (i.e., the solvated polyoxyethylene (150) distearate solution) and C (i.e., polyoxyethylene (150) distearate) of Example 14 were added to the baby shampoo formulation. Composition A was also added to the shampoo bases for comparison. Viscosity in centipoise (cPs) were measured with a Brookfield DVII model viscometer according to standard operating procedures as described above. The viscosity results of the resulting compositions in centipoise are listed below.

TABLE 16B

Uniqema Baby Shampoo Formulation

| Wt. % Composition Added | Viscosity, cPs, for Compositions: | | |
|---|---|---|---|
| | A | B | C |
| 1.0 | 59 | 549 | 84 |
| 2.0 | 142 | 7,534 | 489 |
| 3.0 | 430 | 22,745 | 2,834 |
| 4.0 | 1,275 | 33,473 | 7,203 |

Composition B, i.e., the solvated composition of the present invention, had synergistic thickening over the solvent, i.e., Composition A, alone and the solute, i.e., Composition C, alone.

For comparison, the results of Table 16B are shown below in Table 16C for Compositions B and C on a percent-added polyoxyethylene (150) distearate basis.

TABLE 16C

Uniqema Baby Shampoo Formulation

| Wt. % Composition Added | Wt. % PEG (150) Distearate Added | Viscosity, cPs, for Compositions: | |
|---|---|---|---|
| | | B | C |
| 1.0 | 1.0 | | 84 |
| 2.0 | 2.0 | | 489 |
| 3.0 | 3.0 | | 2,834 |
| 4.0 | 4.0 | | 7,203 |
| 1.0 | 0.2 | 549 | |
| 2.0 | 0.4 | 7,534 | |
| 3.0 | 0.6 | 22,745 | |
| 4.0 | 0.8 | 33,473 | |

Composition B showed unexpected results over Composition C, as noted by the viscosity increase for the much lower levels of polyoxyethylene (150) distearate.

Example 17

Coconut fatty acid (Prifac 7902, available from Uniqema) is a solid paste at room temperature (25° C. melting point) and is insoluble in water at room temperature. Coconut fatty acid is rich in $C_{12}$ and $C_{14}$ fatty acids at about 55 and about 22 weight percent, respectively, with the balance being predominately heavier ($C_{16}$ and $C_{18}$) fatty acids. The Coconut fatty acid was heated to 50° C. to melt the coconut fatty acid, and combined with PPG-2 hydroxyethyl cocamide (Promidium CO product available from Uniqema), a liquid a room temperature, at various proportions. Solvated, clear and homogeneous compositions were observed at varying combinations. No water was required for salvation. The results are shown below in Table 17A.

TABLE 17A

| PPG-2 hydroxyethyl cocamide, Wt. Parts | Coconut fatty acid, Wt. Parts | Weight Ratio[(1)] Wt./Wt. | Appearance after 1 Day at Room Temperature (25° C.) |
|---|---|---|---|
| 15 | 5 | 3/1 | clear liquid |
| 10 | 5 | 2/1 | clear liquid |
| 10 | 10 | 1/1 | clear liquid |
| 5 | 10 | 1/2 | crystals |

[(1)]Weight Ratio of PPG-2 hydroxyethyl cocamide to coconut fatty acid

Clear homogeneous solutions were observed at weight ratios of PPG-2 hydroxyethyl cocamide to coconut fatty acid of about one and greater (i.e., greater amounts of PPG-2 hydroxyethyl cocamide). At a weight ratio of PPG-2 hydroxyethyl cocamide to coconut fatty acid of about one to two, a homogeneous liquid was not observed.

The clear liquids solutions of Table 17A were then cooled to about 5° C. for twenty-four hours. Crystallization and/or solidification was observed at this cooled temperatures. When these cooled samples were warmed to room temperature, i.e., were allowed to thaw, clear homogeneous liquid samples were again observed. These "freezing/thawing" results are shown below in Table 17B.

TABLE 17B

| PPG-2 hydroxyethyl cocamide, Wt. Parts | Coconut fatty acid, Wt. Parts | Weight Ratio[(1)] Wt./Wt. | Appearance after 1 Day | |
|---|---|---|---|---|
| | | | first at 5° C. | then at 25° C. |
| 15 | 5 | 3/1 | paste, some small crystals | clear liquid |
| 10 | 5 | 2/1 | paste, some small crystals | clear liquid |
| 10 | 10 | 1/1 | solid, white | clear liquid |

[(1)]Weight Ratio of PPG-2 hydroxyethyl cocamide to coconut fatty acid

Example 18

Lauric acid (92-94%) (Prifrac 2920, available from Uniqema) is a solid at room temperature (41° C. melting point) and is rich in $C_{12}$ fatty acids, typically about 92%. Lauric acid (98-100%) (Prifrac 2922, available from Uniqema) is a solid at room temperature (43° C. melting point) and is rich in $C_{12}$ fatty acids, typically about 98%. Palmitic acid (Prifrac 2960, available form Uniqema) is a solid at room temperature (60° C. melting point) and is rich in $C_{16}$ fatty acid, typically about 92%. The fatty acids was heated to 50° C. to melt them, and combined with PPG-2 hydroxyethyl cocamide and the isostearamide/nonisostearamide solvent (Composition A of Examples 1-14) at various proportions. Solvated, clear and homogeneous compositions were observed at varying combinations. No water was required for solvation. The results are shown below in Table 18A.

TABLE 18A

| PPG-2 hydroxyethyl cocamide, Wt. Parts | Lauric acid (92-94%), Wt. Parts | Appearance after 1 Day at 20° C. |
|---|---|---|
| 80 | 20 | pourable, clear liquid |
| 50 | 50 | solid |

TABLE 18B

| PPG-2 hydroxyethyl cocamide, Wt. Parts | Lauric acid (98-100%), Wt. Parts | Appearance after 1 Day at 20° C. |
|---|---|---|
| 80 | 20 | pourable, clear liquid |
| 50 | 50 | solid |

TABLE 18C

| PPG-2 hydroxyethyl cocamide, Wt. Parts | Palmitic acid, Wt. Parts | Appearance after 1 Day at 20° C. |
|---|---|---|
| 80 | 20 | solid |
| 50 | 50 | solid |

TABLE 18D

| Composition A, Wt. Parts | Lauric acid (92-94%), Wt. Parts | Appearance after 1 Day at 20° C. |
|---|---|---|
| 80 | 20 | pourable, clear liquid |
| 50 | 50 | solid |

TABLE 18E

| Composition A, Wt. Parts | Lauric acid (98-100%), Wt. Parts | Appearance after 1 Day at 20° C. |
|---|---|---|
| 80 | 20 | pourable, clear liquid |
| 50 | 50 | solid |

TABLE 18F

| Composition A, Wt. Parts | Palmitic acid, Wt. Parts | Appearance after 1 Day at 20° C. |
|---|---|---|
| 80 | 20 | solid |
| 50 | 50 | solid |

Example 19

This example shows enhanced emulsification with the use of solvated nonionic surfactants of the present invention as compared to use of nonsolvated nonionic surfactants. A first emulsion was prepared with 15.00 weight percent mineral oil (white), 2.25 weight percent nonionic surfactant and 82.75 weight percent water. The surfactant used was a blend of 43 weight percent polyoxyethylene (2) stearyl ether (Brij 72, available from Uniqema) and 57 weight percent polyoxyethylene (21) stearyl ether (Brij 721, available form Uniqema), and the blend had a HLB value of about 10.9. After three weeks of storage at room temperature, the emulsion had 30% cream separation, i.e., an unstable emulsion.

A second emulsion was prepared with 15.00 weight percent mineral oil (white), 2.25 weight percent nonionic surfactant system and 82.75 weight percent water. The surfactant system used was 25 weight percent polyoxyethylene (2) stearyl ether (Brij 72, available from Uniqema) dispersed in 75 weight percent of a solvated solution of 25 weight percent polyoxyethylene (21) stearyl ether (Brij 721, available from Uniqema), 60 weight percent of an alkoxylated alkanolamide composition having 1 part by weight propoxylated hydroxyethyl isostearamide to 3 parts by weight propoxylated hydroxyethyl cocamide (Composition A) and 15 weight percent water. This surfactant system has a calculated HLB of 12.5. After three weeks of storage at room temperature, the emulsion was 100% stable, i.e., no separation was observed.

Example 20

Polyoxyethylene (150) distearate (Composition C) (Estol 3734, available from Uniqema) was combined with PPG-2 hydroxyethyl cocamide (Promidium CO product available from Uniqema), and water at the proportions described below and according to the procedures described above to form a solvated, clear and homogeneous composition. The results are shown below in Table 20.

TABLE 20

| polyoxyethylene (150) distearate, Wt. % | PPG-2 hydroxyethyl cocamide, Wt. % | Water, Wt. % | Appearance at 20° C. |
|---|---|---|---|
| 50 | 20 | 30 | clear, soluble, pourable |

While there have been described what are presently believed to be the preferred embodiments of the invention, those skilled in the art will realize that changes and modifications may be made thereto without departing from the spirit of the invention, and it is intended to include all such changes and modifications as fall within the true scope of the invention.

What is claimed is:

1. A homogenous liquid and readily flowable at room temperature composition obtained by solvating:
   a) polyoxyethylene (150) distearate, in an amount from about 10 wt % to 80 wt % based on the total composition; with
   b) from 20 wt % to 80 wt % based on the total composition of at least one alkoxylated fatty alkanolamide; and
   c) optionally water.

2. The composition of claim 1 wherein the alkoxylated fatty alkanolamide is represented by Formula 1;

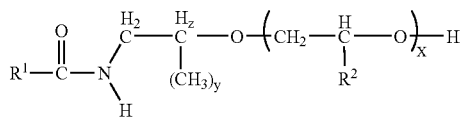

wherein $R^1$ is a branched or straight chain, saturated or unsaturated $C_3$-$C_{21}$ alkyl radical, or a combination thereof; $R^2$ is a $C_1$-$C_2$ alkyl radical or a combination thereof; x is from about 1 to about 8; y is 0 or 1; and z is 1 or 2.

3. The composition of claim 1 wherein the alkoxylated fatty alkanolamide is selected from the group consisting propoxylated hydroxyethyl isostearamide, propoxylated hydroxyethyl caprylamide, propoxylated hydroxyethyl cocamide, propoxylated hydroxyethyl linoleamide, propoxylated hydroxyethyl soyamide, and combinations thereof.

4. The composition of claim 1 wherein the alkoxylated fatty alkanolamide includes propoxylated hydroxyethyl cocamide.

5. The composition of claim 4 wherein the addition of the composition into a cleansing formulation increases viscosity of the cleansing formulation to a greater viscosity than for similar weight additions of unsolvated polyalkylene oxide carboxylic acid diesters into the cleansing formulation.

6. The composition according to claim 1 comprising, when present, from about 5 wt % to about 35 wt % of water.

7. The composition according to claim 1 comprising, when present, from about 5 wt % to about 30 wt % of water.

8. The composition according to claim 1 comprising, when present, from about 10 wt % to about 30 wt % of water.

9. A homogenous liquid and readily flowable at room temperature composition consisting of:
   a) polyoxyethylene (150) distearate, in an amount from about 10 wt % to 80 wt % based on the total composition;
   b) from 20 wt % to 80 wt % based on the total composition of at least one alkoxylated fatty alkanolamide; and
   c) from about 5 wt. % to about 35 wt % based on the total composition of water;
   wherein said composition is obtained by solvating component a) with components b) and c).

10. The composition according to claim 9 comprising from about 10 wt % to about 30 wt % of water.

11. An homogenous liquid and readily flowable at room temperature composition consisting of:
   a) polyoxyethylene (150) distearate, in an amount from about 10 wt % to 80 wt % based on the total composition; and b) from 20 wt % to 80 wt % based on the total composition of at least one alkoxylated fatty alkanolamide; and c) optionally water;

wherein said composition is obtained by solvating component a) with components b) and, if present, c).

12. An homogenous liquid and readily flowable at room temperature thickener composition comprising:
   a) polyoxyethylene oxide carboxylic acid diester, in an amount from about 20 wt % to 70 wt % based on the total composition; and
   b) from 15 wt % to 50 wt % based on the total composition of an alkoxylated fatty alkanolamide comprising propoxylated hydroxyethyl cocamide; and
   c) water.

13. The composition of claim 12 wherein the polyalkylene oxide carboxylic acid diester has a polyethylene oxide moiety corresponding to the formula of —$(OCH_2CH_2)_n$, where n is from about 5 to about 200.

14. The composition of claim 12 wherein component
   a) is present in an amount from about 30 wt % to about 60 wt % based on the total composition.

15. The composition of claim 12 wherein component a) is present in an amount from about 45 wt % to about 55 wt % based on the total composition.

16. The composition of claim 12 wherein component b) is present in an amount from 15 wt % to 35 wt % based on the total composition.

17. The composition of claim 12 wherein component c) is present in an amount from about 5 wt % to about 50 wt % based on the total composition.

18. The composition of claim 12 wherein component c) is present in an amount from about 15 wt % to about 40 wt % based on the total composition.

19. The composition of claim 12 wherein component c) is present in an amount from about 25 wt % to about 30 wt % based on the total composition.

20. A homogenous liquid and readily flowable at room temperature composition comprising:
   a) polyoxyethylene (150) distearate, in an amount from about 10 wt % to 80 wt % based on the total composition; with
   b) from 20 wt % to 80 wt % based on the total composition of at least one alkoxylated fatty alkanolamide; and
   c) optionally water.

21. A homogenous liquid and readily flowable at room temperature composition comprising:
   a) from about 10 wt % to about 80 wt % based on the total composition of a room-temperature-solid solute comprising polyoxyethylene (150) distearate; with
   b) from 20 wt % to 80 wt % based on the total composition of at least one alkoxylated fatty alkanolamide; and
   c) from about 5 wt. % to about 35 wt % based on the total composition of water.

22. The composition according to claim 1 consisting of components a), b) and c).

23. The composition according to claim 12 consisting of components a), b) and c).

24. The composition according to claim 20 consisting of components a), b) and c).

25. The composition according to claim 21 consisting of components a), b) and c).

26. An homogenous liquid and readily flowable at room temperature composition consisting of:
   a) polyoxyethylene oxide carboxylic acid diester, in an amount from about 10 wt % to 80 wt % based on the total composition; and
   b) from 10 wt % to 80 wt % based on the total composition of at least one alkoxylated fatty alkanolamide; and
   c) optionally water;
   wherein said composition is obtained by solvating component a) with components b) and, if present, c).

* * * * *